United States Patent
Lai et al.

(10) Patent No.: US 7,205,336 B2
(45) Date of Patent: Apr. 17, 2007

(54) β-SECRETASE INHIBITORS

(75) Inventors: Ming-Tain Lai, Lansdale, PA (US); Ming-Chih Crouthamel, Perkasie, PA (US); Stephen F. Brady, Philadelphia, PA (US)

(73) Assignee: Merck & Co., Inc., Rahway, NJ (US)

( * ) Notice: Subject to any disclaimer, the term of this patent is extended or adjusted under 35 U.S.C. 154(b) by 73 days.

(21) Appl. No.: 10/512,507

(22) PCT Filed: May 14, 2003

(86) PCT No.: PCT/US03/15109

§ 371 (c)(1),
(2), (4) Date: Oct. 26, 2004

(87) PCT Pub. No.: WO03/099202

PCT Pub. Date: Dec. 4, 2003

(65) Prior Publication Data

US 2005/0164953 A1    Jul. 28, 2005

(51) Int. Cl.
*A61K 31/195* (2006.01)
*C07C 229/00* (2006.01)
(52) U.S. Cl. ...................................... 514/563; 562/448
(58) Field of Classification Search .................... None
See application file for complete search history.

(56) References Cited

FOREIGN PATENT DOCUMENTS

WO    WO 89/04833    6/1989
WO    WO 01/00665    1/2001

*Primary Examiner*—Paul A. Zucker
(74) *Attorney, Agent, or Firm*—John C. Todaro; Melvin Winokur

(57) ABSTRACT

The present invention provides compounds that are inhibitors of the proteolytic activity of the enzyme β-secretase, pharmaceutically acceptable salts of the compounds, pharmaceutical compositions comprising the compounds, processes for making the compounds, and methods of using the compounds to treat Alzheimers disease.

13 Claims, No Drawings

β-SECRETASE INHIBITORS

CROSS REFERENCE TO RELATED APPLICATIONS

This application claims priority under 35 U.S.C. § 119(e) from Provisional Application No. 60/381,535, filed May 17, 2002.

BACKGROUND OF THE INVENTION

Alzheimer's disease is a common, chronic neurodegenerative disease, characterized by a progressive loss of memory and sometimes severe behavioral abnormalities, as well as an impairment of other cognitive functions that often leads to dementia and death. It ranks as the fourth leading cause of death in industrialized societies after heart disease, cancer, and stroke. The incidence of Alzheimer's disease is high, with an estimated 2.5 to 4 million patients affected in the United States and perhaps 17 to 25 million worldwide. Moreover, the number of sufferers is expected to grow as the population ages.

A characteristic feature of Alzheimer's disease is the presence of large numbers of insoluble deposits, known as amyloid plaques, in the brains of those affected. Autopsies have shown that amyloid plaques are found in the brains of virtually all Alzheimer's patients and that the degree of amyloid plaque deposition correlates with the degree of dementia (Cummings & Cotman, 1995, Lancet 326:1524–1587). While some opinion holds that amyloid plaques are a late stage by-product of the disease process, the consensus view is that amyloid plaques are more likely to be intimately, and perhaps causally, involved in Alzheimer's disease.

A variety of experimental evidence supports this view. For example, Aβ, a primary component of amyloid plaques, is toxic to neurons in culture and transgenic mice that overproduce Aβ in their brains show significant deposition of Aβ into amyloid plaques as well as significant neuronal toxicity (Yankner, 1990, Science 250:279–282; Mattson et al., 1992, J. Neurosci. 12:379–389; Games et al., 1995, Nature 373:523–527; LaFerla et al., 1995, Nature Genetics 9:21–29). Mutations in the Alzheimer's precursor protein (APP) gene, leading to increased Aβ production, have been linked to heritable forms of Alzheimer's disease (Goate et al., 1991, Nature 349:704–706; Chartier-Harlan et al., 1991, Nature 353:844–846; Murrel et al., 1991, Science 254:97–99; Mullan et al., 1992, Nature Genetics 1:345–347). Injection of the insoluble, fibrillar form of Aβ into monkey brains results in the development of pathology (neuronal destruction, tau phosphorylation, microglial proliferation) that closely mimics Alzheimer's disease in humans (Geula et al., 1998, Nature Medicine 4:827–831). See Selkoe, 1994, J. Neuropathol. Exp. Neurol. 53:438–447 for a review of the evidence that Aβ and amyloid plaques have a central role in Alzheimer's disease.

Aβ, a 39–43 amino acid peptide derived by proteolytic cleavage of APP, is the major component of amyloid plaques (Glenner & Wong, 1984, Biochem. Biophys. Res. Comm. 120:885–890). APP is actually a family of polypeptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525–527; Tanzi et al., 1988, Nature 331:528–530; Kitaguchi et al., 1988, Nature 331:530–532). APP is membrane bound and undergoes proteolytic cleavage by at least two pathways. In one pathway, cleavage by an enzyme known as α-secretase occurs while APP is still in the trans-Golgi secretory compartment (Kuentzel et al., 1993, Biochem J. 295:367–378). This cleavage by α-secretase occurs within the Aβ portion of APP, thus precluding the formation of Aβ. In another proteolytic pathway, cleavage of the $Met_{671}$-$Asp_{672}$ bond (numbered according to the 751 amino acid protein) by an enzyme known as β-secretase occurs. This cleavage by β-secretase generates the N-terminus of Aβ. The C-terminus is formed by cleavage by a second enzyme known as γ-secretase. The C-terminus is actually a heterogeneous collection of cleavage sites rather than a single site since γ-secretase activity occurs over a short stretch of APP amino acids rather than at a single peptide bond. Peptides of 40 or 42 amino acids in length (Aβ40 and Aβ42, respectively) predominate among the C-termini generated by γ-secretase. Aβ42 is more prone to aggregation than Aβ40, is the major component of amyloid plaque (Jarrett et al., 1993, Biochemistry 32:4693–4697; Kuo et al., 1996, J. Biol. Chem. 271:4077–4081), and its production is closely associated with the development of Alzheimer's disease (Sinha & Lieberburg, 1999, Proc. Natl. Acad. Sci. USA 96:11049–11053). The bond cleaved by γ-secretase appears to be situated within a transmembrane domain of APP. It is unclear as to whether the C-termini of Aβ40 and Aβ42 are generated by a single γ-secretase protease with sloppy specificity or by two distinct proteases. For a review that discusses APP and its processing, see Selkoe, 1998, Trends Cell. Biol. 8:447–453.

Much interest has focused on the possibility of inhibiting the development of amyloid plaques as a means of preventing or ameliorating the symptoms of Alzheimer's disease. To that end, a promising strategy is to inhibit the activity of β- and γ-secretase, the two enzymes that together are responsible for producing Aβ. This strategy is attractive because, if the formation of amyloid plaques as a result of the deposition of Aβ is a cause of Alzheimer's disease, inhibiting the activity of one or both of the two secretases would intervene in the disease process at an early stage, before late-stage events such as inflammation or apoptosis occur. Such early stage intervention is expected to be particularly beneficial (see, e.g., Citron, 2000, Molecular Medicine Today 6:392–397).

Various groups have cloned and sequenced cDNA encoding a protein that is believed to be β-secretase (Vassar et al., 1999, Science 286:735–741; Hussain et al., 1999, Mol. Cell. Neurosci. 14:419–427; Yan et al., 1999, Nature 402:533–537; Sinha et al., 1999, Nature 402:537–540; Lin et al., 2000, Proc. Natl. Acad. Sci. USA 97:1456–1460). Hong et al., 2000, Science 290:150–153 determined the crystal structure of the protease domain of human β-secretase complexed with an eight-residue peptide-like inhibitor at 1.9 angstrom resolution. Compared to other human, aspartic proteases, the active site of human β-secretase is more open and less hydrophobic, contributing to the broad substrate specificity of human β-secretase (Lin et al., 2000, Proc. Natl. Acad. Sci. USA 97:1456–1460).

Ghosh et al., 2000, J. Am. Chem. Soc. 122:3522–3523 disclosed two inhibitors of β-secretase, OM99-1 and OM99-2, that are modified peptides based on the β-secretase cleavage site of the Swedish mutation of APP (SEVNL/DAEFR, with "/" indicating the site of cleavage). OM99-1 has the structure VNL*AAEF (with "L*A" indicating the uncleavable hydroxyethylene transition-state isostere of the LA peptide bond) and exhibits a $K_i$ towards recombinant β-secretase produced in *E. coli* of $6.84 \times 10^{-8}$ M$\pm 2.72 \times 10^{-9}$ M. OM99-2 has the structure EVNL*AAEF (with "L*A"

indicating the uncleavable hydroxyethylene transition-state isostere of the LA peptide bond) and exhibits a $K_i$ towards recombinant β-secretase produced in *E. coli* of $9.58×10^{-9}$ M±$2.86×10^{-10}$ M. OM99-1 and OM99-2, as well as related compounds, are described in International Patent Publication WO 01/00665.

SUMMARY OF THE INVENTION

The present invention is directed to compounds that are aspartyl protease inhibitors capable of inhibiting the cleavage of APP by β-secretase. The compounds of the present invention are useful in the treatment of Alzheimer's disease. Pharmaceutical compounds containing the compounds and methods of using the compounds to treat Alzheimer's disease are disclosed.

DETAILED DESCRIPTION OF THE INVENTION

The present invention provides compounds that are inhibitors of the proteolytic activity of the enzyme β-secretase, pharmaceutically acceptable salts of the compounds, pharmaceutical compositions comprising the compounds, processes for making the compounds, and methods of using the compounds to treat Alzheimer's disease.

The compounds of the present invention are useful for treating Alzheimer's disease by inhibiting the activity of β-secretase, thereby preventing the formation of Aβ, thus leading to a lessening of the deposition of plaques in the brains of those treated with the compounds and a lessening of other deleterious effects of Aβ.

The present invention, in one aspect, provides a compound having the following structure (Formula 1):

Formula 1

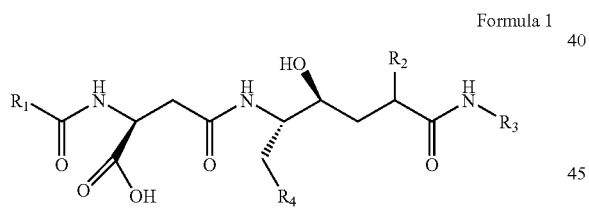

The present invention also provides compounds in which the carbon to which the $R_2$ group is attached is in the R configuration (Formula 2):

Formula 2

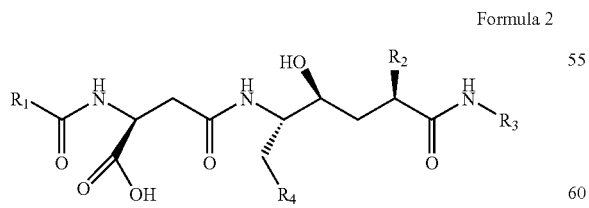

In Formula 1 and Formula 2, $R_1$ is independently selected from the group consisting of: $C_{1-4}$ alkyl, cyclic alkyl, arylalkyl, and aryloxyalkyl.

In certain embodiments, $R_1$ is independently selected from the group consisting of:

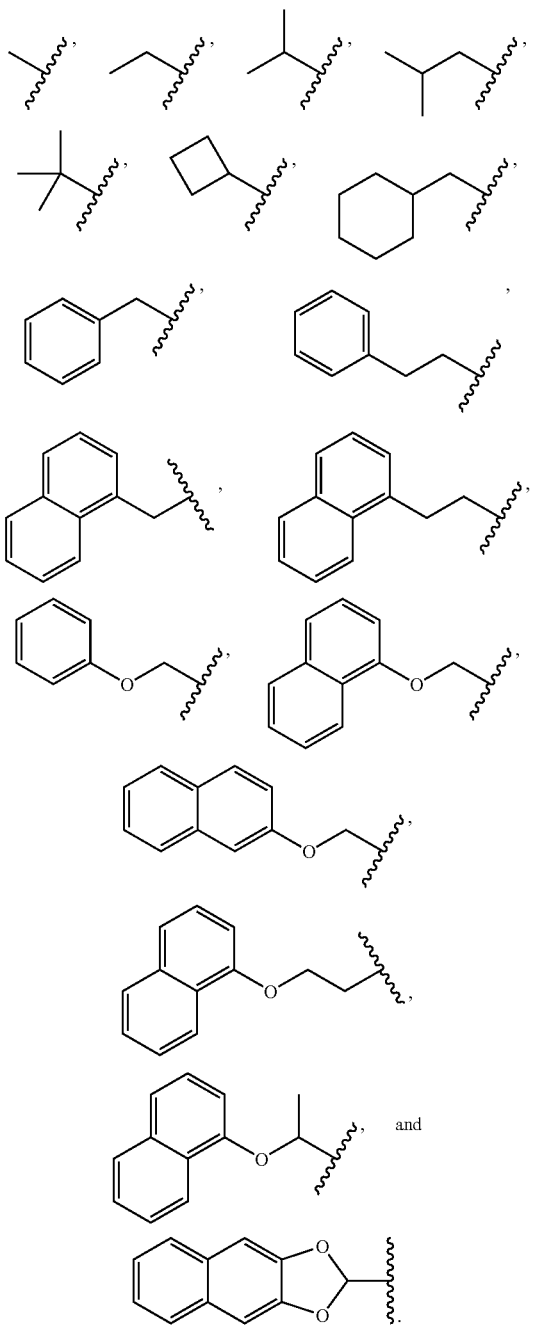

In Formula 1 and Formula 2, $R_2$ is independently selected from the group consisting of: hydrogen, $C_{1-4}$ alkyl, and substituted $C_{1-4}$ alkyl.

In certain embodiments, $R_2$ is independently selected from the group consisting of: hydrogen,

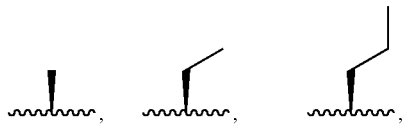

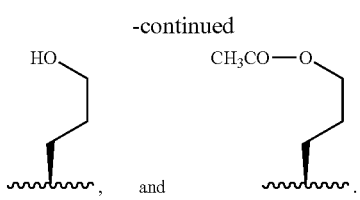

In Formula 1 and Formula 2, $R_3$ is independently selected from the group consisting of: $C_{1-4}$ alkyl, cyclic alkyl, and arylalkyl.

In certain embodiments, $R_3$ is independently selected from the group consisting of:

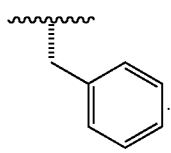

Compounds of Formula 1 can generally be used as β-secretase inhibitors as racemic mixtures of the R and S isomers at the carbon atom to which the $R_2$ group is attached in Formula 1 although it has been found that the R isomer is the active isomer. Therefore, the compounds of Formula 1 are preferably used as pure preparations of the R isomers.

The term "$C_{1-4}$ alkyl" refers to a saturated monovalent hydrocarbon radical, linear or branched, having from 1–4 carbons. Examples are: methyl, ethyl, propyl, isopropyl, butyl, sec-butyl, t-butyl.

The term "substituted $C_{1-4}$ alkyl" refers to a $C_{1-4}$ alkyl substituted with one or more substituents selected from the group consisting of: hydroxyl, acetyloxy, methyloxy, and ethyloxy.

The term "cyclic alkyl" refers to a saturated cyclic hydrocarbon radical having from 4–7 carbons. Preferably, the cyclic alkyl is cyclobutyl, methylenecyclobutyl, cyclopentyl, methylenecyclopentyl, methylenecyclohexyl, cyclohexyl, methylenecycloheptyl, or cycloheptyl.

The term "arylalkyl" refers to an aromatic group selected from phenyl and naphthyl attached to an alkyl group, which alkyl group is in turn attached to Formula 1 or Formula 2 at the $R_1$ or $R_3$ position. The alkyl group may be methylene, ethylene, propylene, n-butylene, or sec-butylene.

The term "aryloxyalkyl" refers to aromatic groups selected from phenyl and naphthyl attached through an oxygen atom to an alkyl group, which alkyl group is in turn attached to Formula 1 or Formula 2 at the $R_1$ position. When the aromatic group includes a fused ring, the link between the fused ring and the oxygen may be at any point along the fused ring. The alkyl group may be methylene, ethylene, propylene, n-butylene, or sec-butylene.

The present invention provides compounds having the following structures:

Formula 3

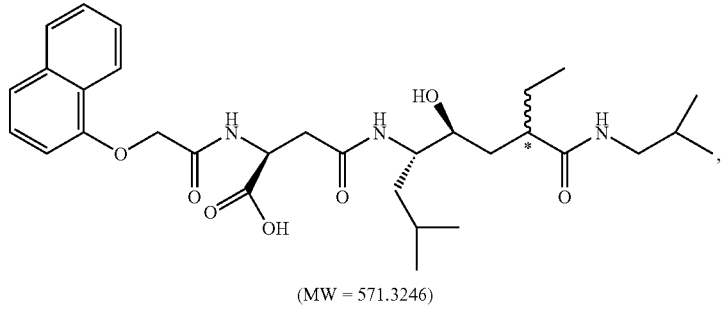

(MW = 571.3246)

Formula 4

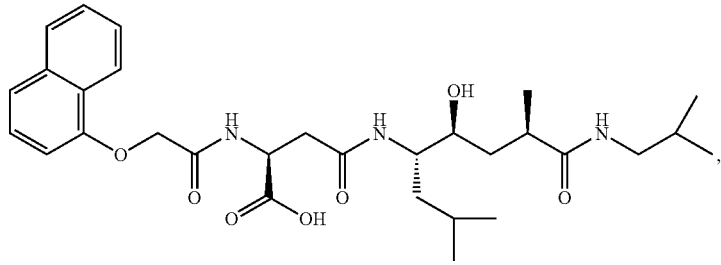

Formula 5

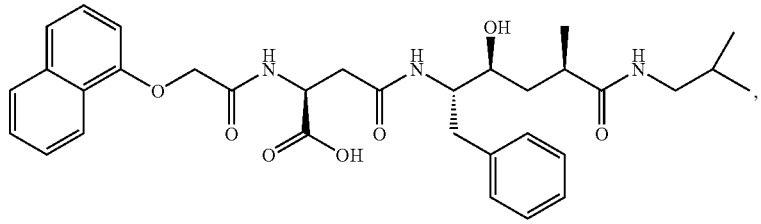

-continued
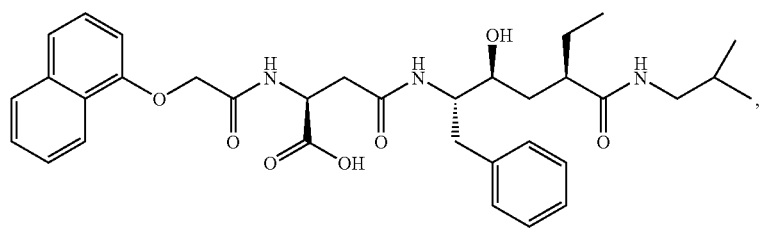
Formula 6
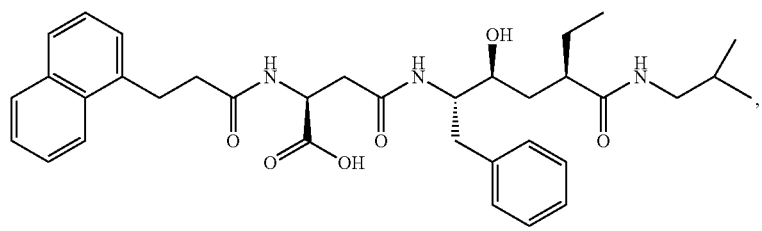
Formula 7
(MW = 553.3152)
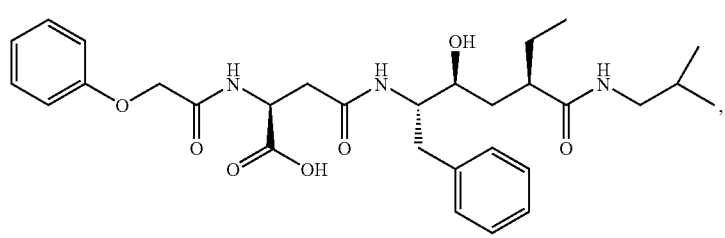
Formula 8
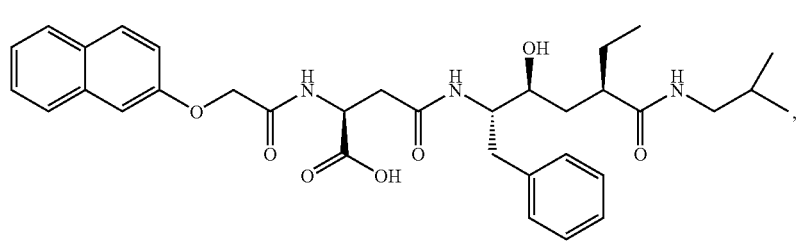
Formula 9
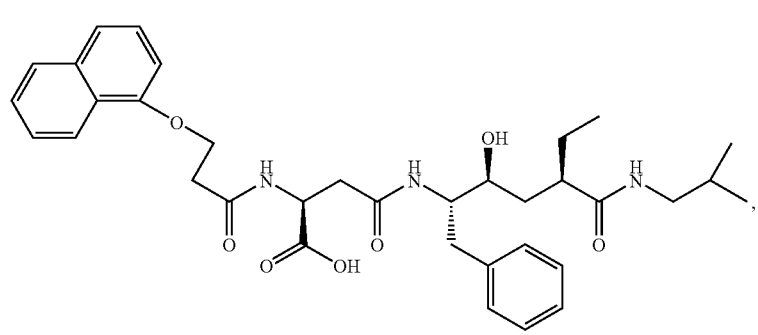
Formula 10
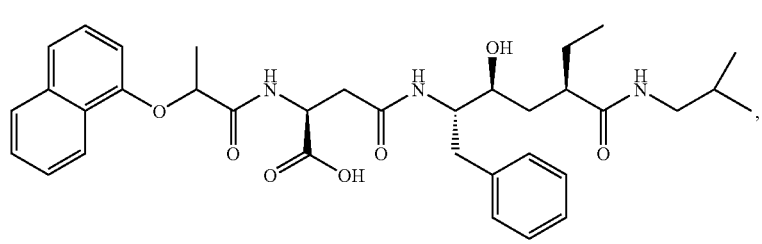
Formula 11

Formula 12
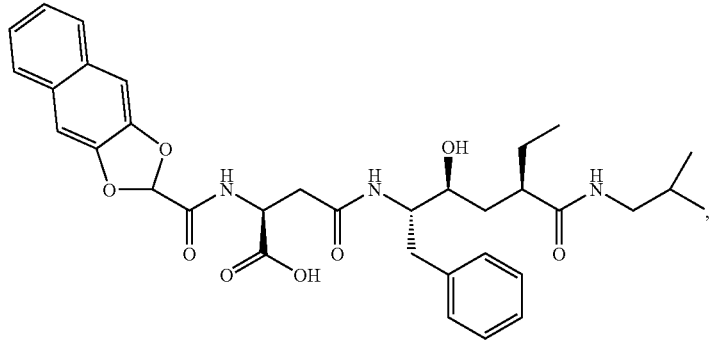
Formula 13
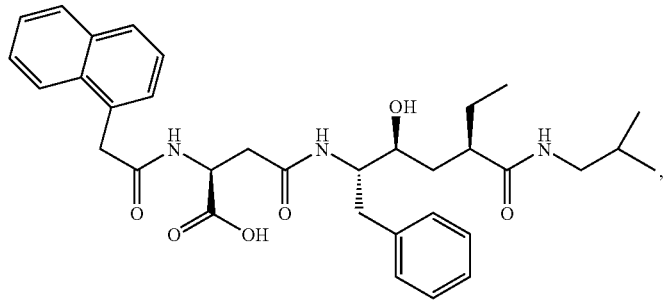
Formula 14
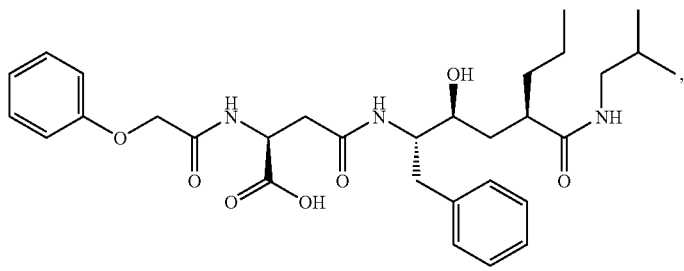
Formula 15
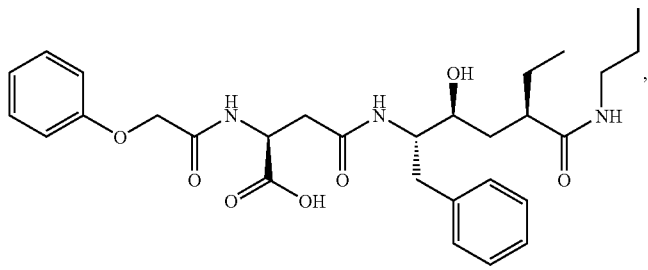
Formula 16
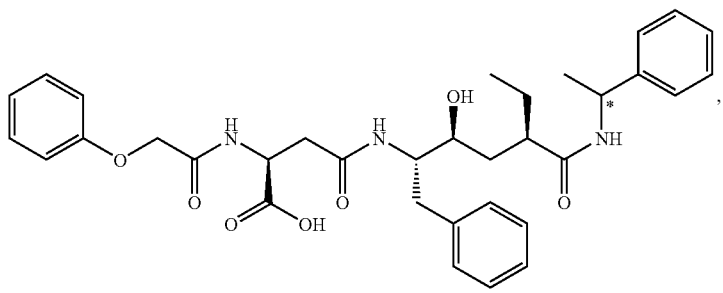

-continued
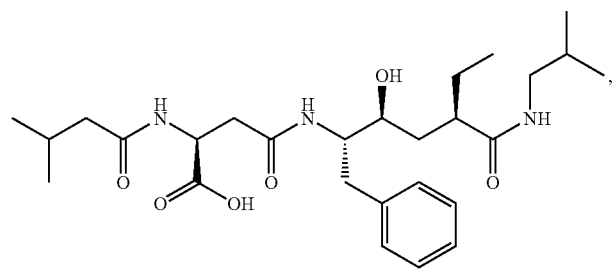
(MW = 505.3152)
Formula 18
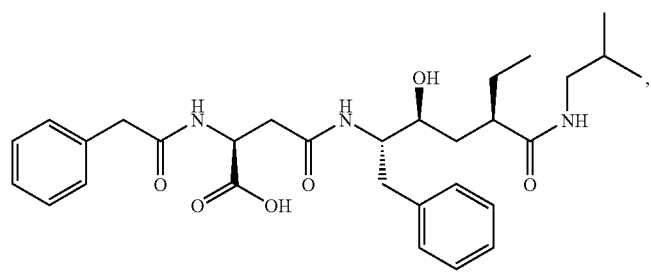
(MW = 539..2995)
Formula 19
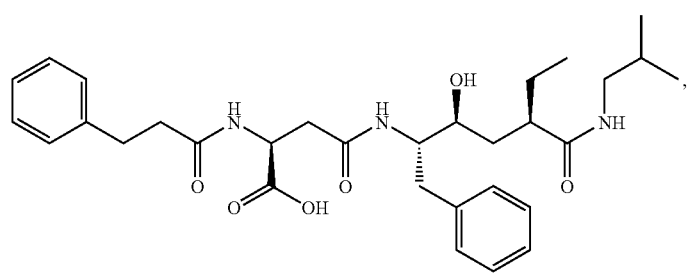
(MW = 553..3152)
Formula 20
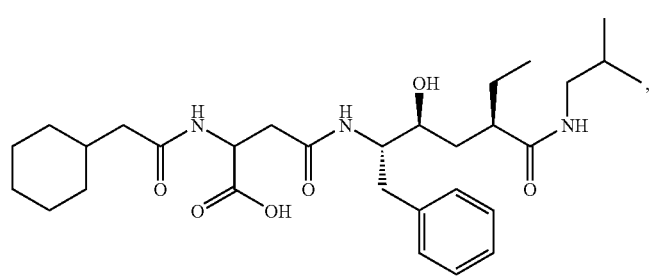
(MW = 545.3465)
Formula 21

Formula 22
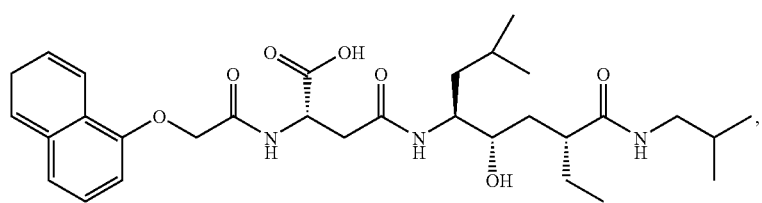
(MW = 571.3242)
Formula 23
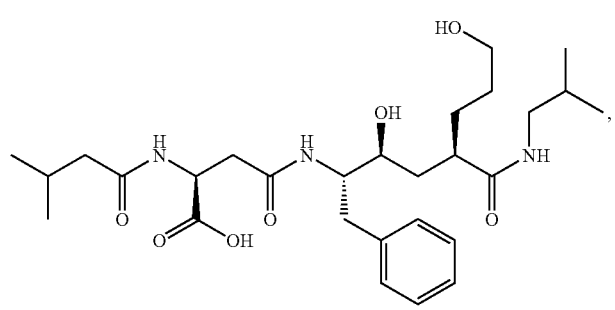
(MW = 535.326)
Formula 24
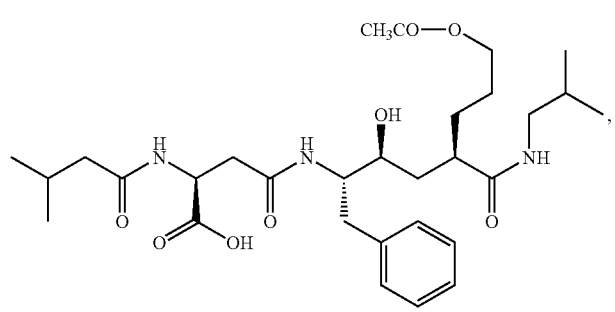
(MW = 577.336)
Formula 25
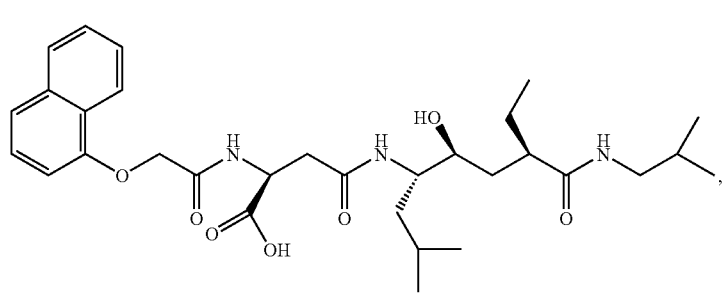
(MW = 477.2829)
Formula 26
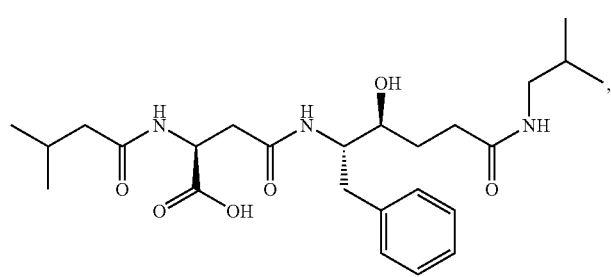
(MW = 477.2829)

-continued
Formula 27
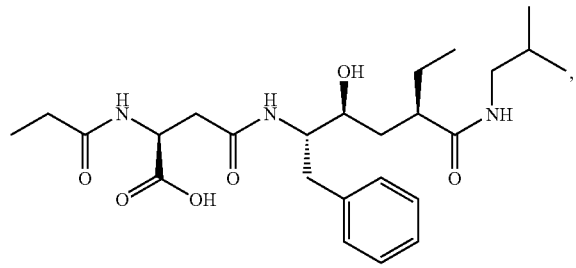
(MW = 477.2839)
Formula 28
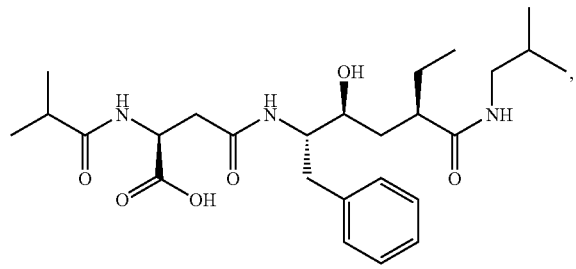
(MW = 491.2995)
Formula 29
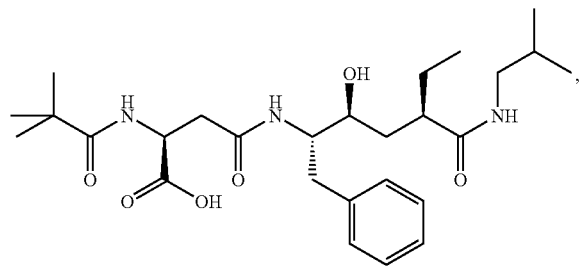
(MW = 505.3152)
Formula 30
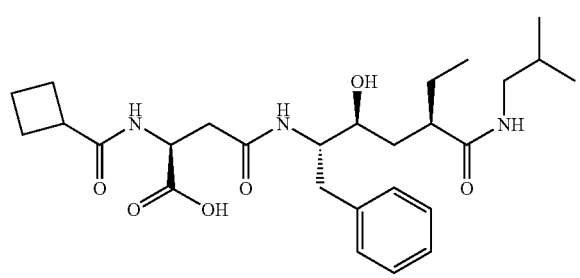
Formula 31
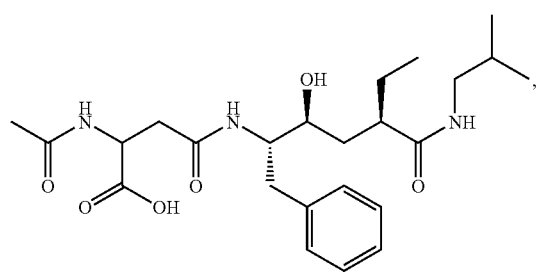
(MW = 463.2673)

-continued

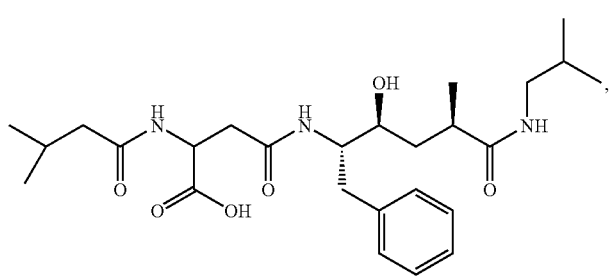

(MW = 491.2995)

Formula 32

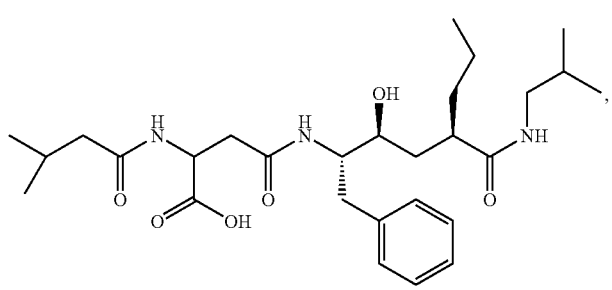

(MW = 519.3308)

Formula 33

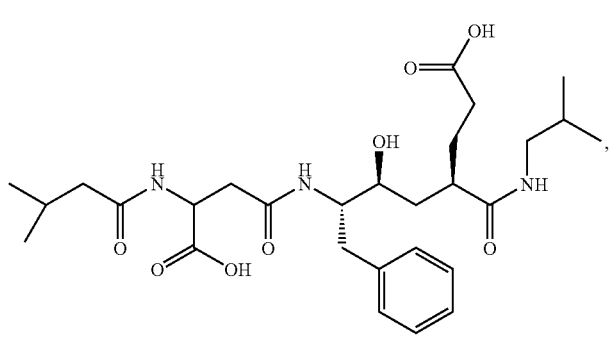

(MW = 549.3050)

Formula 34

The potency of the above-disclosed inhibitors was tested in the FRET assay described in Example 1. The $IC_{50}$ (µM) values ranged from 0.4 to 70.

The present invention includes pharmaceutical compositions comprising one or more compounds of this invention. The compounds of the invention are generally combined with pharmaceutically acceptable carriers to form pharmaceutical compositions. Examples of such carriers and methods of formulation of pharmaceutical compositions containing compounds of the invention and carriers can be found in Gennaro, ed., Remington's Pharmaceutical Sciences, 18$^{th}$ Edition, 1990, Mack Publishing Co., Easton, Pa. Pharmaceutical carriers can include, e.g., conventional tableting ingredients such as corn starch, lacose, sucrose, sorbitol, talc, stearic acid, magnesium stearate, dicalcium phosphate or gums or surfactants such as sorbitan monooleate, polyethylene glycol, and other pharmaceutical diluents, e.g., water, to form a solid preformulation composition containing a homogeneous mixture of a compound of the invention, or a pharmaceutically acceptable salt thereof. To form a pharmaceutically acceptable composition suitable for effective administration, such compositions will contain a therapeutically effective amount of the compounds of the invention.

Therapeutic or prophylactic compositions are administered to an individual in amounts sufficient to treat or prevent Alzheimer's disease or to alleviate the symptoms of Alzheimer's disease. The effective amount can vary according to a variety of factors such as the individual's condition, weight, gender, and age. Other factors include the mode of administration. The appropriate amount can be determined by a skilled physician. Generally, an effective amount will be from about 0.01 to about 1,000, preferably from about 0.1 to about 250, and even more preferably from about 1 to about 50 mg per adult human per day.

Compositions can be used alone at appropriate dosages. Alternatively, co-administration or sequential administration of other agents can be desirable.

The compositions can be administered in a wide variety of therapeutic dosage forms in conventional vehicles for administration. For example, the compositions can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Compositions can be administered in a single daily dose, or the total daily dosage can be administered in divided doses of two, three, four or more times daily. Furthermore, compositions can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compositions is selected in accordance with a variety of factors including age, weight, sex, and medical condition of the patient; the severity of the Alzheimer's disease and other conditions the patient may suffer from; the route of administration; the renal, hepatic, and cardiovascular function of the patient; and the particular composition thereof employed. A physician of ordinary skill can readily determine and prescribe the effective amount of the composition required to prevent, counter or arrest the progress of the Alzheimer's disease. Optimal precision in achieving concentrations of composition within the range that yields efficacy without toxicity requires a regimen based on the kinetics of the composition's availability to the brain. This involves a consideration of the distribution, equilibrium, and elimination of a composition as well as the composition's ability to cross the blood/brain barrier.

Frequently, it will be desirable or necessary to introduce the pharmaceutical compositions containing the compounds of the present invention directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The term "pharmaceutically acceptable salts" refers to salts prepared from pharmaceutically acceptable non-toxic bases or acids, including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

The present invention further provides the use of a compounds of the present invention or a pharmaceutically acceptable salt thereof in the manufacture of a medicament for the treatment, prevention, or alleviation of the symptoms of Alzheimer's disease.

Also disclosed is a method of treatment of a person suffering from or prone to Alzheimer's disease which comprises administering to that person an effective amount of a compound according to the present invention or a pharmaceutically acceptable salt thereof where said effective amount delays the appearance of, delays the progression of, or alleviates the symptoms of Alzheimer's disease.

The present invention further provides the use of a compounds of the present invention or a pharmaceutically acceptable salt thereof in the manufacture of a medicament for the treatment, prevention, or alleviation of the symptoms of Down's syndrome, vascular dementia, mild cognitive impairment, or hereditary cerebral hemmorhage with amyloidosis of the Dutch type, as well as to preventing or delaying the onset of Alzheimer's disease in those who would progress from mild cognitive impairment to Alzheimer's disease.

Also disclosed is a method of treatment of a person which comprises administering to that person an effective amount of a compound according to the present invention or a pharmaceutically acceptable salt thereof where said effective amount delays the appearance of, delays the progression of, or alleviates the symptoms of Down's syndrome, vascular dementia, mild cognitive impairment, or hereditary cerebral hemmorhage with amyloidosis of the Dutch type.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, or gelatin.

The compounds of the present invention have at least one asymmetric center at the carbon atom marked with a star in Formula 3. Additional asymmetric centers may be present depending upon the nature of the various substituents on the compound. Each such asymmetric center will independently produce two optical isomers and it is intended that all of the possible optical isomers and diastereomers in mixtures and as pure or partially purified compounds are included within the ambit of this invention. The most preferred compounds of this invention have the R configuration at the carbon atom marked with a star in Formula 3.

Where the herein-described processes for the preparation of the compounds according to the invention give rise to mixtures of stereoisomers, it may be advantageous to use the racemic mixtures without further purification of individual stereoisomers. For example, the racemic mixture of the compound of Formula 3 is a potent inhibitor even as a racemic mixture of the R and S isomers at the carbon atom marked with a star in Formula 3. Alternatively, it may be desirable to separate stereoisomers. This can be done by conventional techniques such as preparative chromatography.

The absolute stereochemistry of compounds of the present invention may be determined by x-ray crystallography of crystalline products of the compounds or crystalline intermediates which may be derivatized, if necessary, with a reagent containing an asymmetric center of known absolute configuration.

During the synthetic sequences described herein, it may be necessary and/or desirable to protect sensitive or reactive groups on any of the molecules concerned. This may be achieved by means of conventional protecting groups, such as those described in *Protective Groups in Organic Chemistry*, ed. J. P. W. McOmie, Plenum Press, 1973; and *Protective Groups in Organic Synthesis*, T. W. Greene & P. G. M. Wuts, John Wiley & Sons, 1991.

In addition to the assays exemplified herein, a variety of assays for measuring the ability of a substance to inhibit β-secretase activity are known in the art and can be used in connection with the compounds of the present invention. Such assays are described in, e.g., Turner et al., 2001, Biochem. 40:10001–10006; Steinhilb et al., 2001, J. Biol. Chem. 276:4476–4484. Where purified β-secretase is referred to herein, β-secretase is purified by the procedures described in Shi et al., 2001, J. Biol. Chem. 276:10366–10373. The following non-limiting examples are presented to illustrate the invention.

EXAMPLE 1

FRET Assay for Inhibition of β-Secretase Activity

A. Reaction Mixture: (Plate=Costar #3915) volumes are given in μL

| | |
|---|---|
| 25 | NH$_4$OAc, 200 mM pH 4.5.0 |
| 10 | BSA, 1 mg/ml (Bovine Fraction V, Sigma #9647) |
| 10 | EDTA, 150 mM |
| 2 | 10% CHAPS |
| 2 | Deferoxamine Mesylate, 50 mM (Sigma #D9533) |
| 10 | β-secretase, 200 nM in H$_2$O |
| 31 | H$_2$O |
| 8 | Compound to be tested in DMSO |
| 98 | Total |

1. The compound and β-secretase are incubated at room temperature for 30 min with shaking
2. Two microliters of 62.5 μM FRET substrate is added into the solution and the resulting mixtures are incubated at room temperature with shaking for 5 min
3. The kinetic reading on the LJL Analyst AD is taken every 5 min fluorescence intensity; tamraqst-7; excitation 530 nm; emission 580 nm; dichroic mirror rhodamine 561; duration=300 sec, 5 reads)
4. The $K_i$ of the inhibitors are determined by the equation of $((v_0/v_i)-1=[I]/K_i)$. The $v_0$ and $v_i$ represent the initial rate of substrate hydrolysis in the absence and presence of inhibitor ($v_0$, $v_i$), respectively.

Note:
a. β-secretase final concentration=30 nM (If using less, e.g., 2 nM β-secretase, change the reading duration to 3600 sec.)
b. DMSO=10%
c. FRET 12mer final concentration=1.25 μM
d. Hydrolysis<10%
Reader: LJL Analyst AD
Excitation: 530, FWHM 25
Emission: 580, FWHM 10
Dichroic 561

EXAMPLE 2

Additional FRET Assay for Inhibition of β-Secretase Activity

| | |
|---|---|
| PART 1 | |
| 25 μL | 4x NaOAc (200 mM, pH 4.5) |
| 10 μL | 1 mg/ml BSA (Bovine Fraction V, Sigma #9647) |
| 2 μL | 10% CHAPS |
| 2 μL | 50 mM Deferroxamine Mesylate (Sigma #D9533) |
| 10 μL | 150 mM EDTA, pH 4.5 |
| 41 μL | dH$_2$O |
| 10 μL | two inhibitors at different concentrations with fixed ratio |
| transfer 80 μL to part 2; black fluorescence 96-well plate (Costar #3915). | |
| PART 2 | |
| 80 μL | part 1 mixture |
| 18 μL | β-secretase mixture: 5 μL 4x NaOAc, 4.5 |
| | 2 μL 1 mg/mL BSA (0.1%) |
| | 2 μL 150 mM EDTA, 4.5 |
| | 0.4 μL 10% CHAPS |
| | 0.4 μL 50 mM Def. Mes. |
| | 6.1 μL dH$_2$O |
| | 2 μL 0.1 μg/μL β-secretase |
| | (β-secretase diluted in 20 mM TRIS, 7.2; 125 mM NaCl) | incubate for 30 min at room temperature; shaking.
add 2 μL 125 μM FRET substrate. Take a reading every 5 min on the LJL Analyst AD for 20 min (fluorescence intensity; tamra-qst-7; excitation 530 nm; emission 580 nm; rhodamine 561 dichroic mirror).
$V_0/v_i$ were calculated at each inhibitor concentration and plot against the concentration of one of the inhibitors

EXAMPLE 3

Synthesis of the Parent Compound 3 of the Present Invention as the Single Isomeric Constituent 25

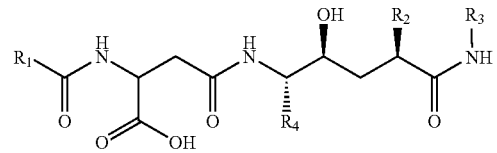

The compound of Formula 25 is the single diastereoisomer at the C-2 (*) corresponding to the isomer mixture 3 as per Formula 1. The starting Fmoc derivative Ia is prepared using a published route (Ghosh, A. K.; Dhin, D.; Downs, D.; Koelsch, G.; Lin, X.; Ermolieff, J.; Tang, J. Design of Potent Inhibitors for Human Brain Memapsin 2 (β-Secretase). 2000, 122, 3522–3523), with the adaptation that for introduction of the ethyl group at C-2 ethyl iodide is employed in the stereoselective alkylation of the lactone intermediate.

Thus, to a solution of 1.0 g (1.8 mmol) of intermediate Ia in 30 ml of DMF is added 0.44 g (2.9 mmol) of HOBt, followed by 0.22 ml (0.16 g, 2.2 mmol) of 2-methylpropylamine incrementally, making sure the pH stays below 7.5 (moistened narrow-range indicator paper). Then 0.56 g (2.9 mmol) of EDC is added, followed by periodic N-methyl morpholine (NMM) to maintain pH 6–7. After 20 hr water is added, the solvent is removed under reduced pressure, and the residue is partitioned with $H_2O$/EtOAc plus dil. $KHSO_4$, washing in turn with $H_2O$, satd $NaHCO_3$, and 50% aq NaCl (2×). After drying ($Na_2SO_4$), the EtOAc is removed under reduced pressure and the product is purified by silica gel column chromatography, eluting with EtOAc/hexane to isolate intermediate IIa as a colorless oil (LC-MS, NMR).

A solution of 115 mg (0.19 mmol) of intermediate IIa in 20 ml of EtOAc is cooled to −20° and saturated with HCl gas. Saturation is maintained at a temperature of 0° for 20–30 min, followed by purging of the solution with $N_2$ for 1–2 hr. The solvent is then removed under reduced pressure, and the residue is dried under vacuum for 1 hr and dissolved in 6 ml of DMF, followed by 3 ml of piperidine. After 10 min the solvent is removed under reduced pressure, 20 ml of DMF is added, the DMF is removed under vacuum, and the DMF addition/removal procedure is repeated twice, followed by drying under high vacuum for 2 hr. To a solution of this residue in 6 ml of DMF is added 73 mg (0.23 mmol) of Boc-aspartic acid α-benzyl ester, followed by 43 mg (0.32 mmol) of HOBt and enough NMM to bring the pH to 7.5. Then 65 mg (0.34 mmol) of EDC is introduced and the reaction mixture is stirred for 20 hr, followed by addition of $H_2O$ and extractive workup with EtOAc as above. Solvent removal under reduced pressure and addition of ether affords 70 mg of intermediate IIIa as a white solid (TLC, LC-MS).

A solution of intermediate IIIa in 20 ml of EtOAc is treated with HCl gas exactly as described above, except saturation is maintained for only 10 min before purging with $N_2$. The residue after drying under vacuum is dissolved in 6 ml of DMF, to which are added 29 mg (0.15 mmol) of 1-naphthyloxyacetic acid and 28 mg (0.21 mmol) of HOBt, then sufficient NMM (approx. 0.05 ml) to bring the pH to 7.5. To the solution is added 41 mg (0.21 mmol) of EDC, followed by stirring for 20 hr with addition of NMM as needed to maintain pH 7. Workup proceeds as described above for the isolation of intermediate IIIa, and the crude coupling product is dissolved in 25 ml of 95% EtOH and hydrogenated at atmospheric pressure (balloon reservoir) with 36 mg of 10% Pd-on-carbon for 1 hr. After filtration through Celite and concentration under reduced pressure, the crude product is purified by preparative HPLC on a C18 column using a gradient of 0.1% aq. $NH_4HCO_3$/$CH_3CN$. Lyophilization affords 30 mg of compound 25 (LC-MS, HPLC, N), identical with the active diastereoisomer of the C-2 isomeric mixture 3.

EXAMPLE 4

Synthesis of Compound 8 of the Present Invention

The starting Boc derivative Ib is prepared using a published route (Ghosh, A. K.; Dhin, D.; Downs, D.; Koelsch, G.; Lin, X.; Ermolieff, J.; Tang, J. Design of Potent Inhibitors for Human Brain Memapsin 2 (β-Secretase). 2000, 122, 3522–3523), with the adaptation that Boc-phenylalanine is employed as the starting material for incorporation of the benzyl group at C-5, and ethyl iodide is employed in the stereoselective alkylation of the lactone intermediate for introduction of the ethyl group at C-2.

Thus, to a solution of 0.19 g (0.41 mmol) of intermediate Ib in 6 ml of DMF is added 0.089 g (0.59 mmol) of HOBt, followed by 0.058 ml (0.042 g, 0.58 mmol) of 2-methylpropylamine. Then 0.12 g (0.62 mmol) of EDC is added, followed by incremental NMM to maintain pH 7.5. After 20 hr water is added, the solvent is removed under reduced pressure, and the residue is partitioned with $H_2O$/EtOAc plus dil. $KHSO_4$, washing in turn with $H_2O$, satd $NaHCO_3$, and 50% aq NaCl (2×). After drying ($Na_2SO_4$), the EtOAc is removed under reduced pressure, followed by drying under vacuum to afford intermediate IIb as a colorless oil (LC-MS).

A solution of 192 mg (0.37 mmol) of intermediate IIb in 20 ml of EtOAc is cooled to −20° and saturated with HCl gas. Saturation is maintained at a temperature of 0° for 30 min, followed by purging of the solution with $N_2$ for 1–2 hr. The solvent is then removed under reduced pressure, and the residue is dried under vacuum for 1 hr and dissolved in 9 ml of DMF, followed by addition of 10 μl of NMM. To this solution is added 159 mg (0.49 mmol) of Boc-aspartic acid α-benzyl ester, followed by 106 mg (0.79 mmol) of HOBt and enough NMM to bring the pH to 7.5. Then 146 mg (0.76 mmol) of EDC is introduced and the reaction mixture is stirred for 20 hr, followed by addition of $H_2O$ and extractive workup with EtOAc as above. Solvent removal under reduced pressure and addition of ether affords 186 mg of intermediate IIIb as a white solid (TLC, LC-MS).

A solution of intermediate IIIb in 30 ml of EtOAc is treated with HCl gas exactly as described above, except saturation is maintained for only 10 min before purging with $N_2$. The residue after drying under vacuum is dissolved in 12.0 ml of DMF, to which are added 78 mg (0.51 mmol) of HOBt and sufficient NMM (approx. 0.045 ml) to bring the pH to 7.0. To 2.0 ml of this stock solution (one-sixth of the total) is added 9.2 mg (0.061 mmol) of phenoxyacetic acid, followed by 17.4 mg (0.09 mmol) of EDC. After stirring for 20 hr, the reaction is processed as described above for the isolation of intermediate IIIb, and the crude coupling product is dissolved in 15 ml of 95% EtOH and hydrogenated at atmospheric pressure (balloon reservoir) with 30 mg of 10% Pd-on-carbon for 2 hr. After filtration through Celite and concentration under reduced pressure, the crude product is purified by preparative HPLC on a C18 column using a gradient of 0.1% aq. $NH_4HCO_3$/$CH_3CN$. Lyophilization affords 15 mg of compound 8 (LC-MS, HPLC).

EXAMPLE 5

Synthesis of Other Compounds of the Present Invention

Compounds of Formulas 4–24 and 26–31 were prepared by employing the methodology of Examples 3 and 4, substituting the appropriate starting materials where necessary.

Given the guidance above, and combined with methods well known in the art, one of skill in the art would be able to choose appropriate starting materials in order to readily synthesize the compounds of Formulas 4–24 and 26–31 as well as other compounds within the scope of the present invention that are not specifically exemplified herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various publications are cited herein, the disclosures of which are incorporated by reference in their entireties.

What is claimed is:

1. A compound of Formula 1 or a pharmaceutically acceptable salt thereof:

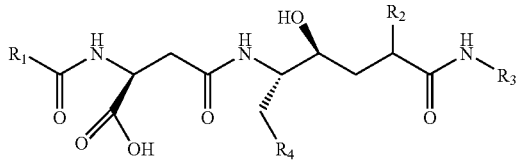

wherein:
R₁ is independently selected from the group consisting of: $C_{1-4}$ alkyl, cyclic alkyl, arylalkyl, and aryloxyalkyl;
R₂ is independently selected from the group consisting of: hydrogen,

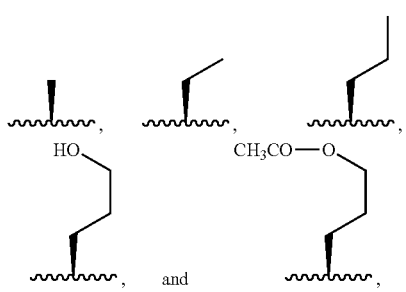

R₃ is independently selected from the group consisting of: $C_{1-4}$ alkyl, cycloalkyl, and arylalkyl;
and R₄ is independently selected from the group consisting of: $C_{1-4}$ alkyl and arylalkyl.

2. The compound of claim 1 wherein:
R₁ is independently selected from the group consisting of:

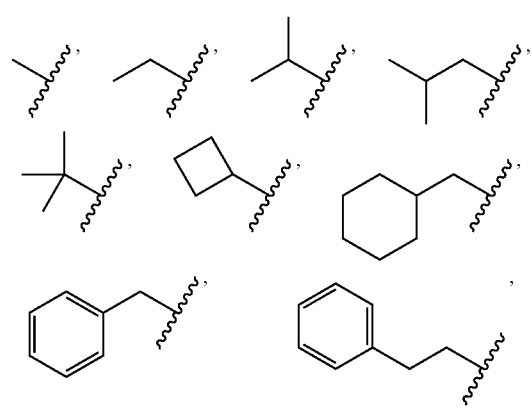

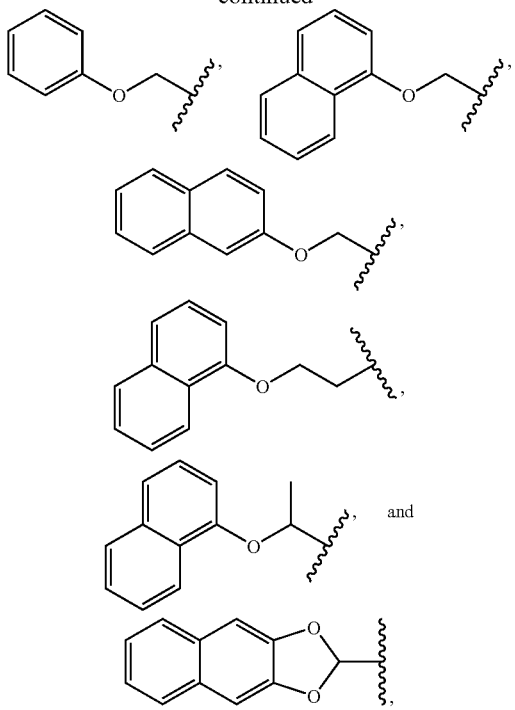

3. The compound of claim 1 wherein;
R₃ is independently selected from the group consisting of:

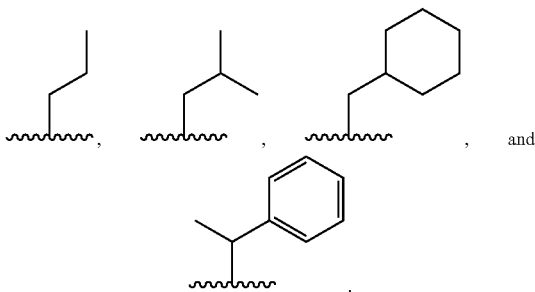

4. The compound of claim 1 wherein:
R₄ is independently selected from the group consisting of:

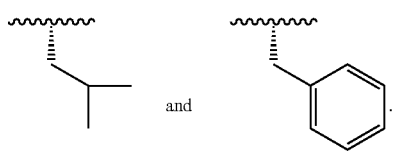

5. The compound of claim 1 wherein:
R₁ is independently selected from the group consisting of:

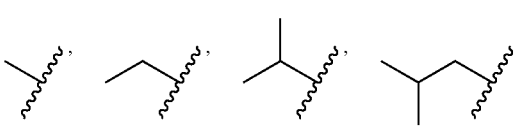

-continued

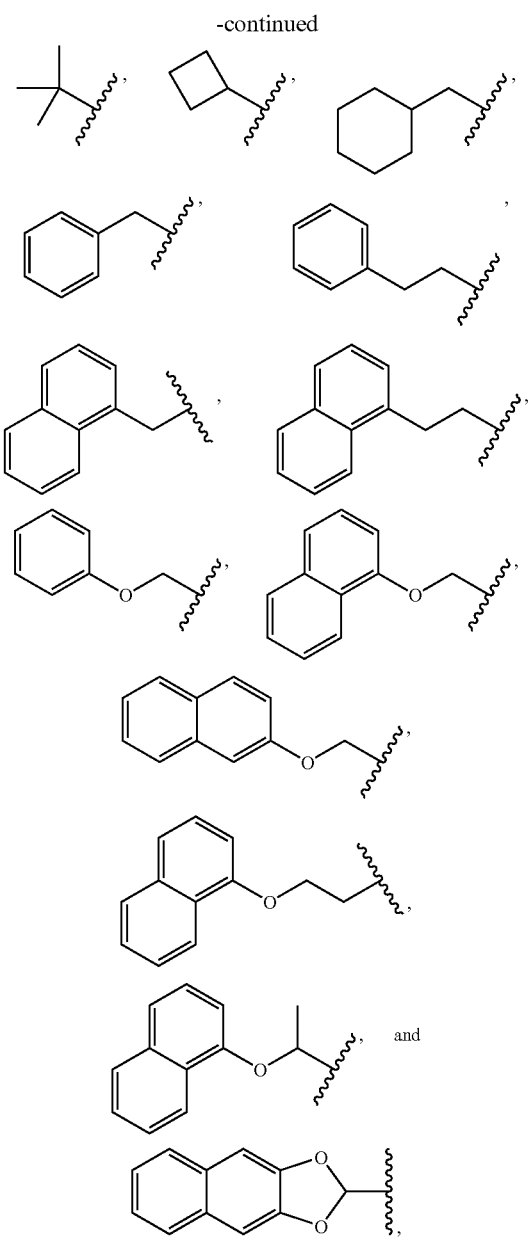

$R_3$ is independently selected from the group consisting of:

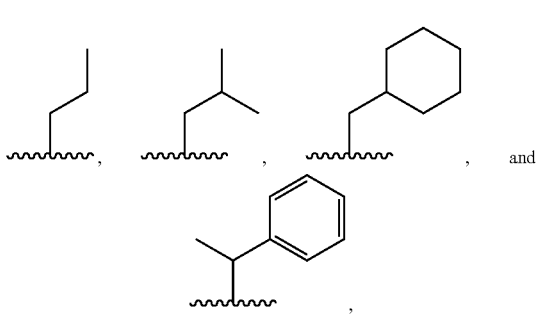

and $R_4$ is independently selected from the group consisting of:

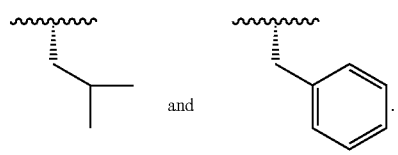

6. A compound of Formula 2 or a pharmaceutically acceptable salt thereof:

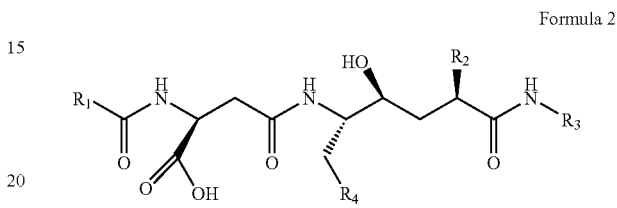

Formula 2 wherein:
$R_1$ is independently selected from the group consisting of: $C_{1-4}$ alkyl, cyclic alkyl, arylalkyl, and aryloxyalkyl;
$R_2$ is independently selected from the group consisting of: hydrogen,

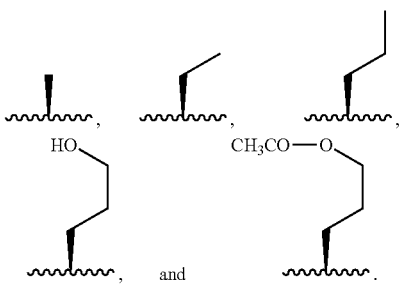

$R_3$ is independently selected from the group consisting of: $C_{1-4}$ alkyl, cycloalkyl, and arylalkyl;
and $R_4$ is independently selected from the group consisting of: $C_{1-4}$ alkyl and arylalkyl.

7. The compound of claim 6 wherein:
$R_1$ is independently selected from the group consisting of:

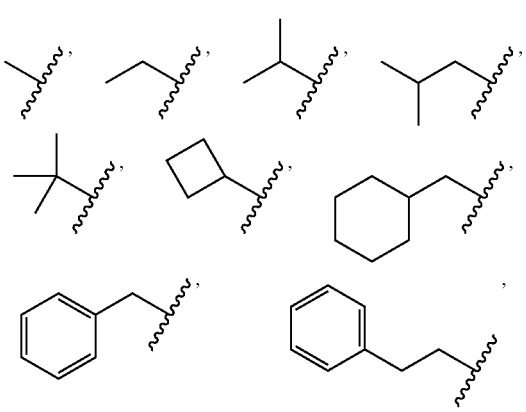

-continued

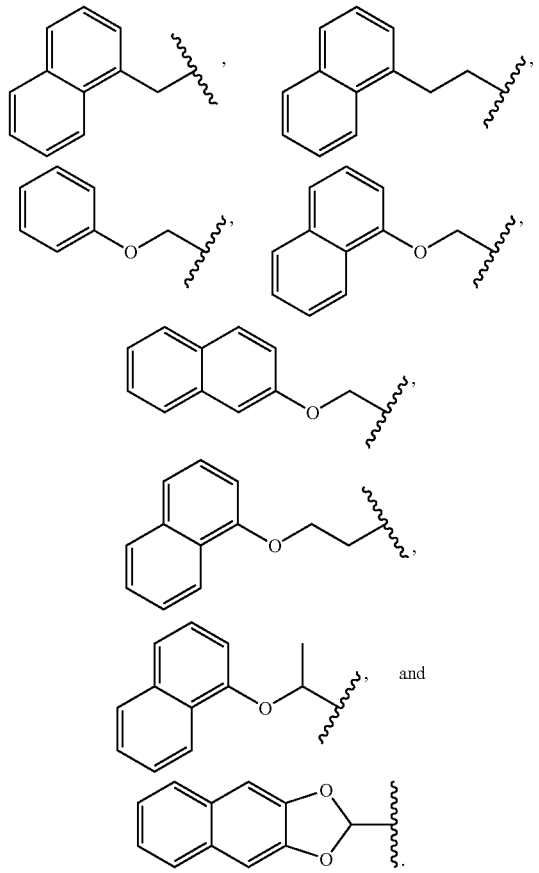

8. The compound of claim 6 wherein:
$R_3$ is independently selected from the group consisting of:

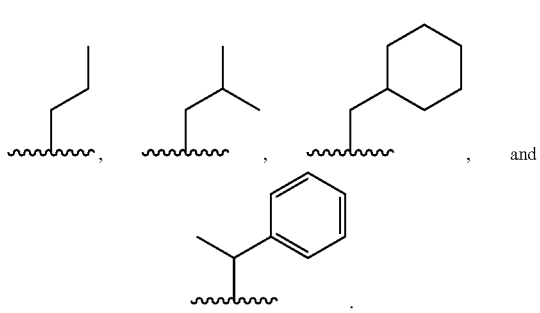

9. The compound of claim 6 wherein:
$R_4$ is independently selected from the group consisting of:

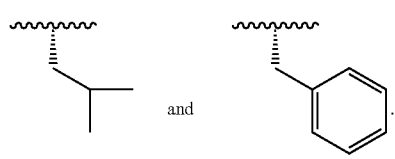

10. The compound or pharmaceutically acceptable salt thereof of claim 6 wherein:

$R_1$ is independently selected from the group consisting of:

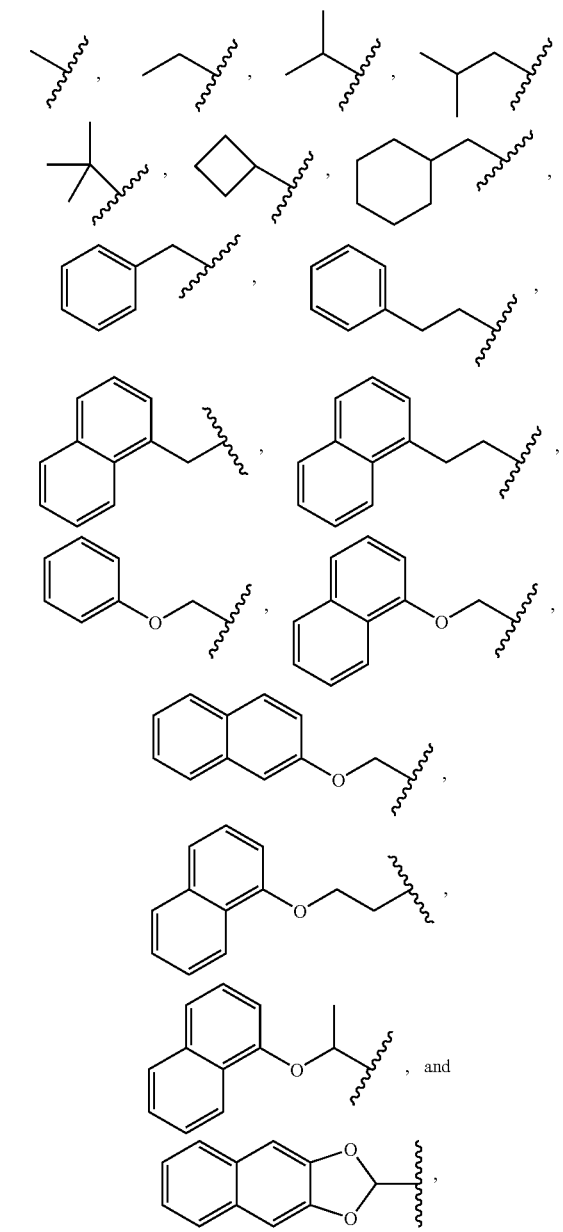

$R_3$ is independently selected from the group consisting of:

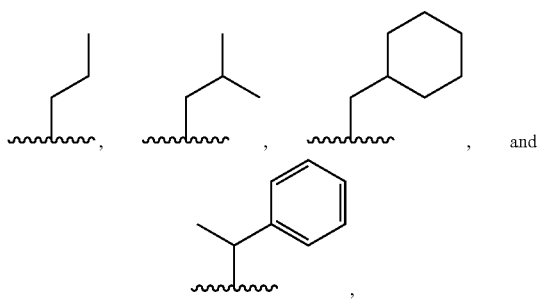

and $R_4$ is independently selected from the group consisting of:

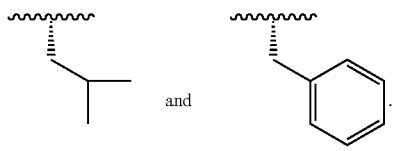
and
5
11. A compound which is selected from the group consisting of:
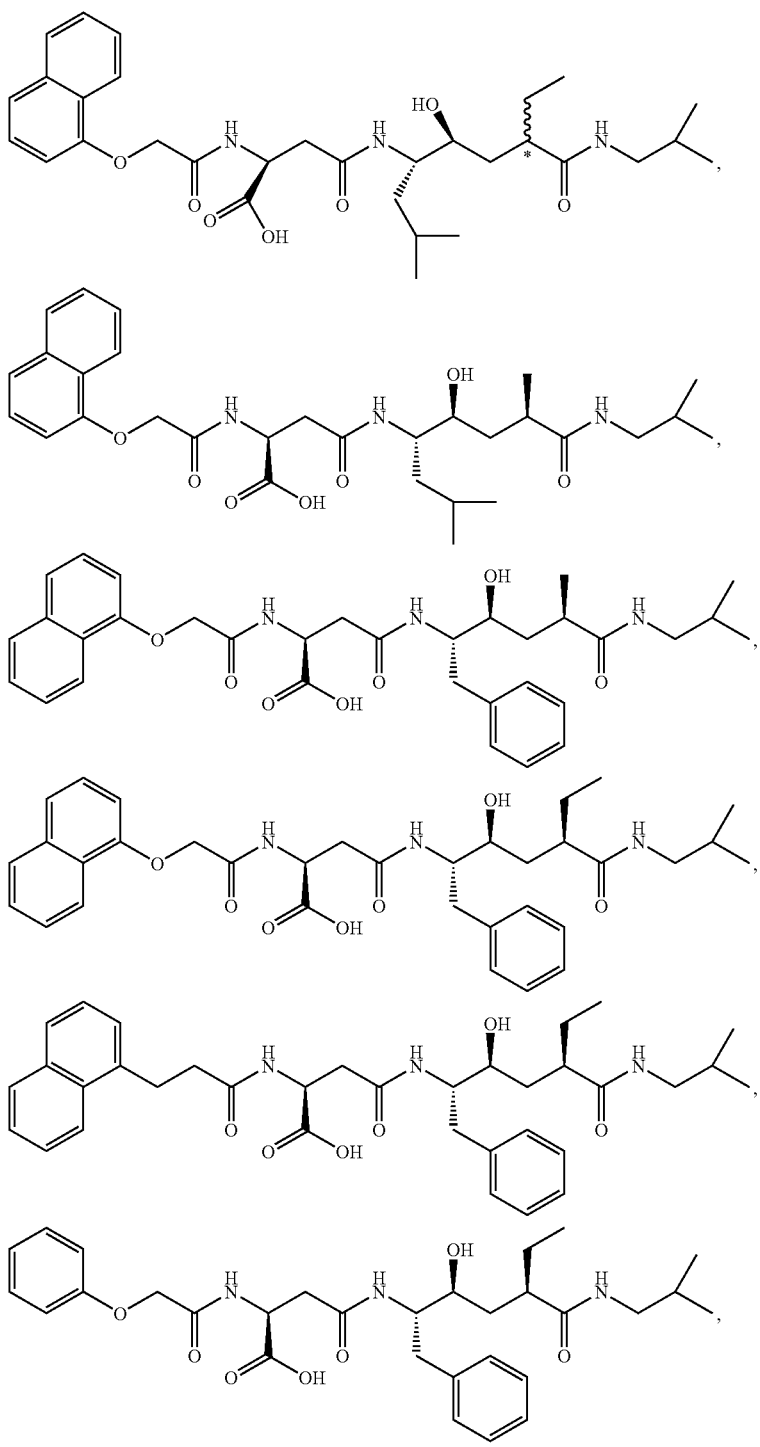

-continued
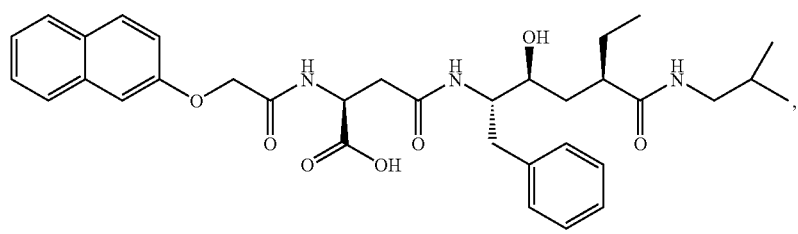
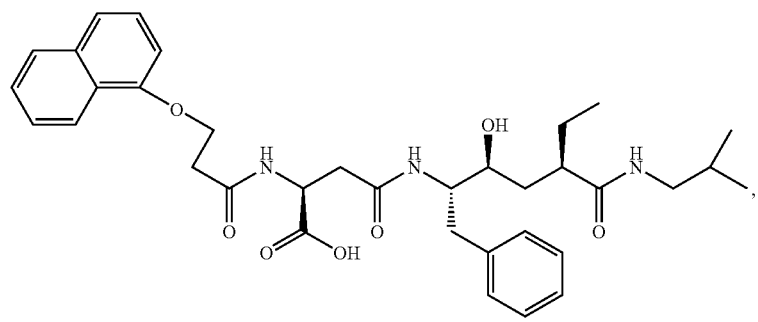
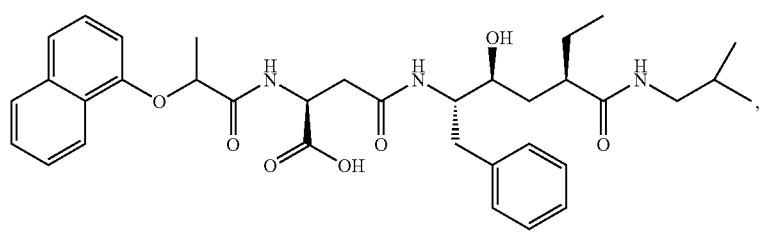
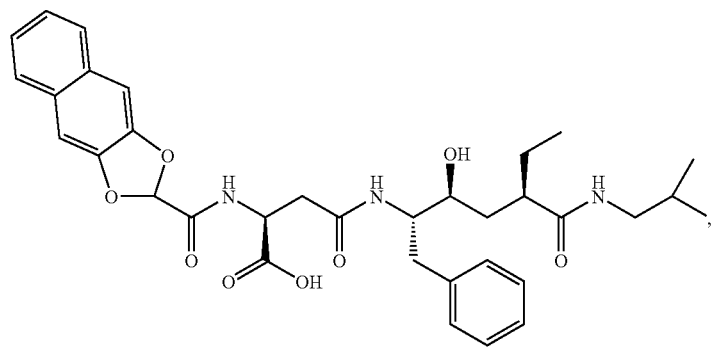
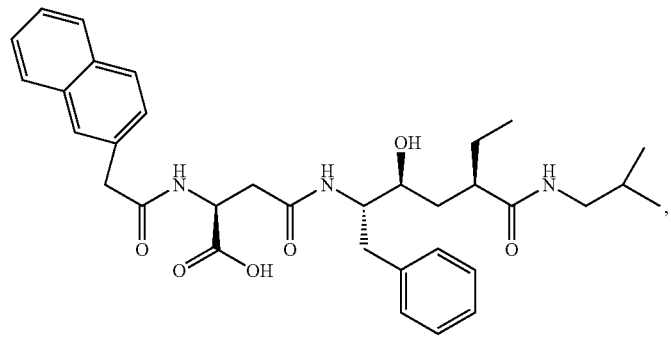

-continued
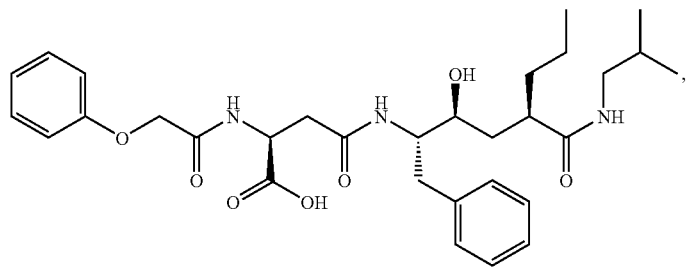
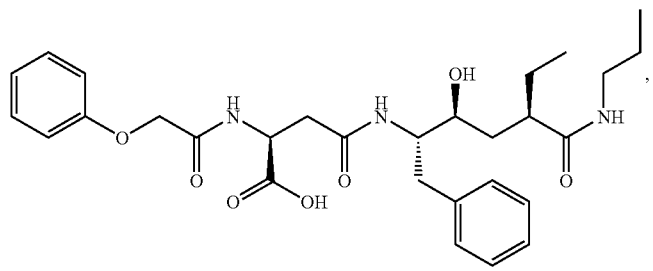
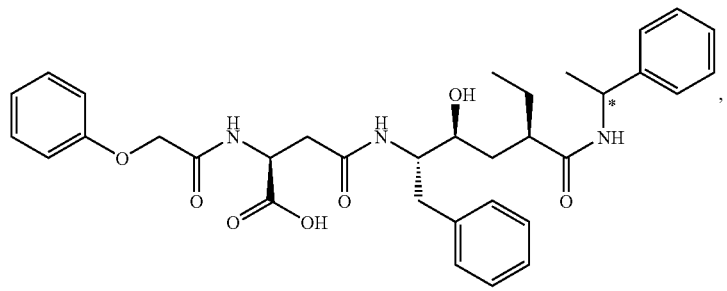
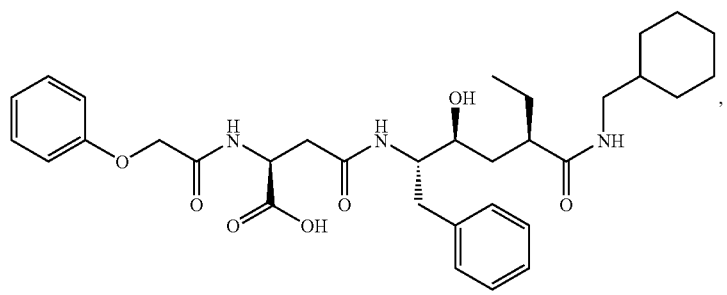
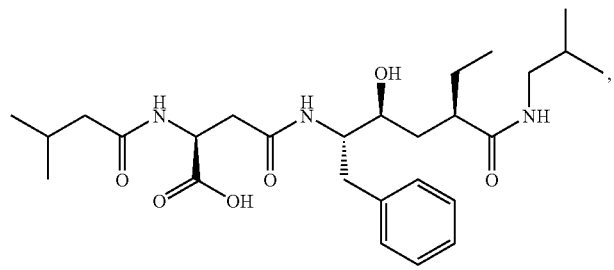
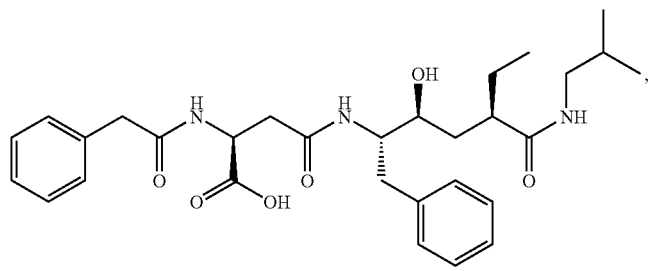

-continued
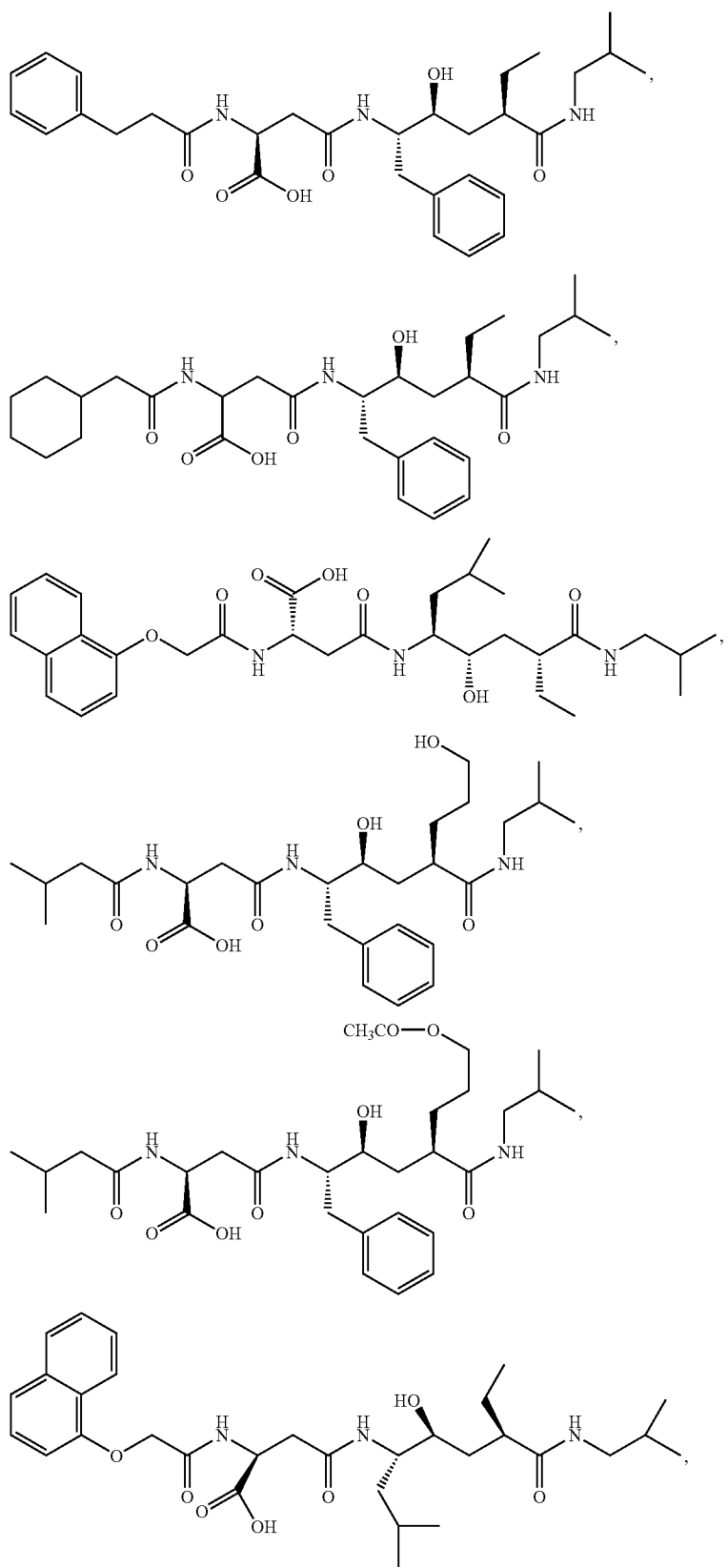

-continued

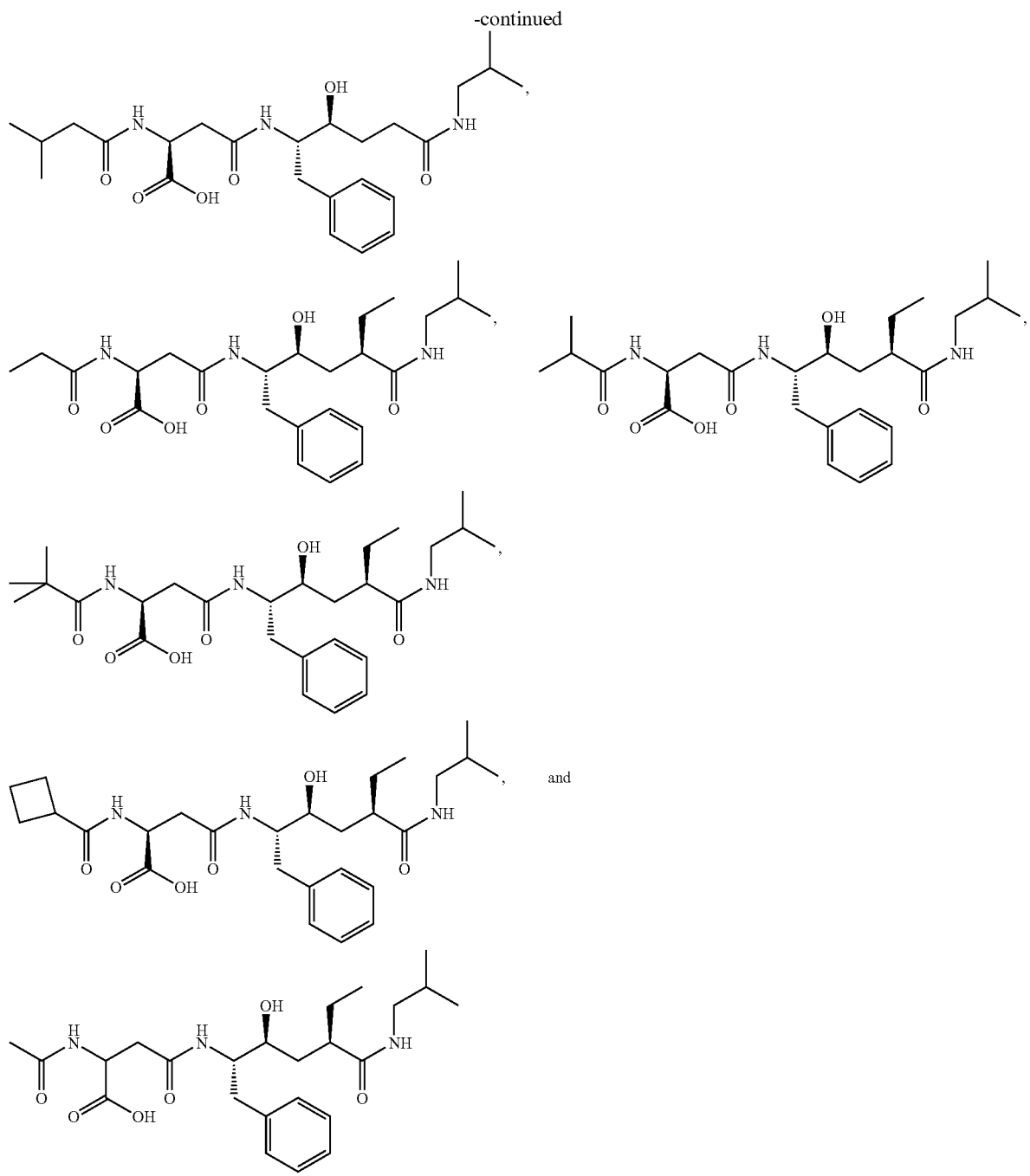

or a pharmaceutically acceptable salt thereof.

12. A pharmaceutical composition comprising a compound of claim 1 or a pharmaceutically acceptable salt thereof and a pharmaceutically acceptable carrier.

13. A method for the treatment of a person suffering from or prone to Alzheimer's disease comprising administering to that person an effective amount of a compound of claim 1 or a pharmaceutically acceptable salt thereof.

* * * * *